US011355029B2

(12) United States Patent
Vuillerme et al.

(10) Patent No.: US 11,355,029 B2
(45) Date of Patent: Jun. 7, 2022

(54) METHOD AND SYSTEM FOR ESTIMATING A DEMAND OR AN ATTENTIONAL COST ASSOCIATED WITH THE EXECUTION OF A TASK OR ATTENTION SHARING STRATEGIES DEVELOPED BY AN INDIVIDUAL (71) Applicants: UNIVERSITÉ GRENOBLE ALPES, Saint Martin d'Hères (FR); CENTRE HOSPITALIER UNIVERSITAIRE DE GRENOBLE, La Tronche (FR)

(72) Inventors: Nicolas Vuillerme, Saint Martin d'Hères (FR); Petra Hlavackova, Saint Martin d'Hères (FR); Bruno Diot, Mercurey (FR); Anthony Fleury, Douai (FR)

(73) Assignees: UNIVERSITÉ GRENOBLE ALPES, Saint Martin d'Hères (FR); CENTRE HOSPITALIER UNIVERSITAIRE DE GRENOBLE, La Tronche (FR)

( * ) Notice: Subject to any disclaimer, the term of this patent is extended or adjusted under 35 U.S.C. 154(b) by 692 days.

(21) Appl. No.: 16/088,005

(22) PCT Filed: Mar. 23, 2017

(86) PCT No.: PCT/EP2017/056921
§ 371 (c)(1),
(2) Date: Feb. 21, 2019

(87) PCT Pub. No.: WO2017/162789
PCT Pub. Date: Sep. 28, 2017

(65) Prior Publication Data
US 2019/0172367 A1  Jun. 6, 2019

(30) Foreign Application Priority Data
Mar. 24, 2016  (FR) ...................................... 1652541

(51) Int. Cl.
*G09B 19/00* (2006.01)
*A61B 5/11* (2006.01)
(Continued)

(52) U.S. Cl.
CPC .......... *G09B 19/003* (2013.01); *A61B 5/1126* (2013.01); *A61B 5/168* (2013.01);
(Continued)

(58) Field of Classification Search
CPC .... G09B 19/003; G09B 7/00; G09B 19/0038; G09B 7/02; G16H 50/20; A61B 5/1126; A61B 5/168
(Continued)

(56) References Cited

U.S. PATENT DOCUMENTS 4,028,819 A * 6/1977 Walker ..................... A61B 5/16
434/258
8,529,448 B2 * 9/2013 McNair ................ A61B 5/7203
600/301

(Continued)

FOREIGN PATENT DOCUMENTS

WO  WO2017162789 A1  9/2017

OTHER PUBLICATIONS

Foreign Communication from a Related Counterpart—International Search Report and Written Opinion, dated Apr. 24, 2017, PCT/EP2017/056921, filed Mar. 23, 2017.
(Continued)

*Primary Examiner* — Robert P Bullington
*Assistant Examiner* — Stephen Alvesteffer (57) ABSTRACT

The invention relates to a method for estimating the attentional resources invoked for execution of a primary task and/or attention sharing strategies developed by an individual, said method being implemented in a mobile terminal, being based on utilization of the dual-task paradigm, and
(Continued)

comprising the following steps: Evaluation of first performance ratings of the individual during the execution of a primary task alone, Evaluation of second performance ratings of the individual during the execution of a secondary task alone, Evaluation of third performance ratings of the individual during the simultaneous execution of the primary and secondary tasks, Estimation of the attentional demand required for the execution of the primary task and/or of the effect (beneficial or negative) of a secondary task on the control mechanisms involved in the execution of the primary task and/or attention sharing strategies developed by an individual by comparing the first, second, and third performance ratings.

13 Claims, 1 Drawing Sheet

(51) Int. Cl.
    *A61B 5/16*     (2006.01)
    *G09B 7/02*     (2006.01)
    *G09B 7/00*     (2006.01)
    *G16H 50/20*     (2018.01)

(52) U.S. Cl.
    CPC ............ *G09B 7/00* (2013.01); *G09B 7/02* (2013.01); *G09B 19/0038* (2013.01); *G16H 50/20* (2018.01)

(58) Field of Classification Search
    USPC ........................................................ 434/247
    See application file for complete search history.

(56) References Cited

U.S. PATENT DOCUMENTS

| | | | |
|---|---|---|---|
| 8,764,532 B1 | 7/2014 | Berme | |
| 9,842,511 B2* | 12/2017 | Smyth | G09B 19/00 |
| 2010/0092929 A1* | 4/2010 | Hallowell | G09B 7/00 434/167 |
| 2012/0046569 A1* | 2/2012 | Johnstone | A61B 5/16 600/544 |
| 2015/0019266 A1* | 1/2015 | Stempora | G06Q 40/08 705/4 |
| 2015/0038803 A1* | 2/2015 | Uhlig | A61B 5/4023 600/301 |
| 2015/0332004 A1* | 11/2015 | Najafi | G16H 50/20 706/46 |
| 2016/0262680 A1* | 9/2016 | Martucci | G09B 7/00 |
| 2017/0270818 A1* | 9/2017 | French | G09B 19/003 |

OTHER PUBLICATIONS

Kosse, Nienke M., et al., "Validity and Reliability of Gait and Postural Control Analysis Using the Tri-axial Accelerometer of the iPod Touch," Annals of Biomedical Engineering, Springer US, New York, vol. 43, No. 8, Dec. 31, 2014 (Dec. 31, 2014), pp. 1935-1946, XP035516431. ISSN: 0090-6964, DOI: 10.1007/S10439-014-1232-0 [retrieved on Dec. 31, 2014].

* cited by examiner

METHOD AND SYSTEM FOR ESTIMATING A DEMAND OR AN ATTENTIONAL COST ASSOCIATED WITH THE EXECUTION OF A TASK OR ATTENTION SHARING STRATEGIES DEVELOPED BY AN INDIVIDUAL

CROSS-REFERENCE TO RELATED APPLICATIONS

This application is a filing under 35 U.S.C. 371 as the National Stage of International Application No. PCT/EP2017/056921, filed Mar. 23, 2017, entitled "METHOD AND SYSTEM FOR ESTIMATING A DEMAND OR AN ATTENTIONAL COST ASSOCIATED WITH THE EXECUTION OF A TASK OR ATTENTION SHARING STRATEGIES DEVELOPED BY AN INDIVIDUAL," and which claims the benefit of and priority to France Application No. 1652541, filed with the Intellectual Property Office of France on Mar. 24, 2016, both of which are incorporated herein by reference in their entirety for all purposes.

FIELD OF THE INVENTION

The present invention relates to the field of the estimation of performance ratings associated with the execution of one (or several) task(s) by an individual.

More precisely, the invention relates to a method comprising a dual-task protocol used to estimate attentional resources or costs needed for their execution or to determine the attention sharing strategies developed by an individual (prioritization sequentialization of the tasks).

A dual-task situation is defined by the simultaneous performance of two tasks, a task referred to as "primary task", and an added task referred to as "secondary task".

The primary and secondary tasks may consist of a proprioceptive task, or a motor task, or a perceptive task, or a postural task, or a locomotion task, or a spatial orientation task or a functional task, or a cognitive task, or a visuo-motor tracking task, or a visuo-manual pointing task, or a pedalling task, etc.

The invention has advantageously numerous applications, notably in the specialities associated with the evaluation, with the diagnosis, with the monitoring, with the learning, with the re-education, with the training, or with the improvement of the perceptive, postural, locomotion, motor, spatial orientation or functional capacities of young and elderly people,
of people afflicted with developing or chronic sickness,
of people in a handicap and/or dependency situation,
of people having suffered a traumatism, an injury, an accident, etc.

DESCRIPTION OF THE PRIOR ART

Context

The execution of a primary task—such as maintaining balance whilst standing up or the control of walking—generally speaking, mobilizes/consumes attentional resources in individuals.

The mobilization/consumption of the attentional resources associated with the execution of the same task may furthermore depend on a certain number of factors relating, amongst other things, to the individual performing this task (for example: their age, their build, their state of health, their level of skill, their sensori-motor and cognitive capacities, their affective and emotional state, their level of vigilance and distraction, their state of physical and psychological tiredness, etc.), the task to be carried out (for example: nature and complexity of the task, etc.), the physical environment in which this task is carried out (for example: availability and precision of the sensory information, situations of inter-sensory conflicts, etc.), or else the voluntary attention applied to the task (for example: priority setting).

Numerous works bear witness to the interest shown by researchers, clinicians and practitioners in the links between postural and motor activities and attentional cognitive functions, in particular in the framework of the prediction and of the prevention of falls for an elderly person.

The document U.S. Pat. No. 8,764,532 describes a system based on the dual-task principle in order to predict the risks of a fall for an individual. The system comprises:

a rotating mobile support designed to accommodate a patient,
a screen for the display of a task,
a measurement unit for the acquisition of data notably relating to the posture of the patient, to a reaction time of the patient in response to a stimulus, etc., and
a processing unit for predicting a risk of a fall or of concussion based on the data measured by the measurement unit.

This system, based on the dual-task principle, uses an interactive game and/or a virtual reality scenario and/or an immersive graphics environment controlled by the movement of a subject in order to evaluate the probability that the subject has of falling and/or whether they have suffered a concussion.

Such a system has numerous drawbacks. On the one hand, the complexity of setting up the device renders the use of the latter unacceptable. On the other hand, the installation of the device overall is laborious and cannot be implemented by the patient themselves.

However, dual-task situations—which consist in carrying out two tasks at the same time—are common in everyday life. Thus, in daily life, balance or locomotion tasks must therefore be controlled efficiently in conjunction with the execution of other tasks that are cognitive and/or motor in nature (memorizing, discussion, control of precise movements, acquiring information).

There accordingly exists a need for a system based on the dual-task principle that can be used under conditions close to those encountered in the daily life of the individual—which differ from clinical or laboratory conditions.

Another drawback of this system is that it does not allow the exercises to be adapted according to the patient being treated (for example, their sensori-motor and cognitive capacities).

At the current time, no system exists that is simple to implement and allows an individual to evaluate the attentional resources or costs employed during the execution of a perceptive, postural, locomotion, motor, spatial orientation or functional task or the attention sharing strategies developed by an individual to be determined. More precisely, no system exists that is designed to be used alone in complete autonomy without support or assistance from a third party.

One aim of the invention is to provide a method based on the use of the dual-task paradigm allowing an individual to evaluate the attentional resources or costs needed for the execution of a perceptive, postural, locomotion, motor, spatial orientation or functional task or to determine the attention sharing strategies developed by an individual. Another aim of the invention is to enable an evaluation of the cognitive capacities via the execution of a certain number of tasks (reaction time, mental arithmetic task, spatial memory task, etc.).

The present invention allows an individual to be assisted, for example and in a non-limiting manner:
in the detection of cognitive disorders, and/or
in the prediction of risk of a fall, and/or
in the framework of a re-education in order to re-teach them to (re-)automate a task, and/or
in the prevention of a fall

SUMMARY OF THE INVENTION

For this purpose, the invention provides a method for estimating an attentional demand or cost associated with the execution of a task or of an attention sharing strategy developed by an individual, the said method being implemented in a mobile terminal and being based on the use of the multi-task paradigm, noteworthy in that it comprises the following steps:

a) Evaluation of first performance ratings of the individual during the execution of at least one primary task, the evaluation step including the sub-steps consisting in:
Generating a first type of visual and/or audio and/or touch-sensitive information on the terminal, the said information including instructions relating to the primary task to be carried out,
Measuring a plurality of first data values during the execution of the primary task,
Determining an actual movement of the individual with processing means of the mobile terminal, the actual movement being determined based on the measured first data values during the execution of the primary task, b) Evaluation of second performance ratings of the individual during the execution of at least one secondary task, the evaluation step including the sub-steps consisting in:
Generating a second type of visual and/or audio and/or touch-sensitive information on the terminal, the said information including instructions relating to the secondary task to be carried out,
Collecting second data values representing the response of the individual during the execution of the secondary task, c) Evaluation of third performance ratings of the individual during the simultaneous execution of the primary task and of the secondary task, the evaluation step including the sub-steps consisting in:
Generating a third type of visual and/or audio and/or touch-sensitive information on the terminal, the said information including instructions relating to the simultaneous execution of the primary and secondary tasks,
Measuring third data values relating to the execution of the primary and secondary tasks, d) Comparison of the first, second and third performance ratings evaluated during the steps a) to c):
for estimating the attentional demand required for the execution of the primary task and/or
for estimating the effect (beneficial or negative) of a secondary task on the control mechanisms involved in the execution of the primary task and/or
for estimating an attention sharing strategy developed by the individual.

The use of the primary task allows a quantification of the postural, motor, locomotion capacities. The use of the secondary task allows a quantification of the cognitive capacities. The use of a dual-task protocol allows:
attentional resources or costs needed for their execution to be estimated or
attention sharing strategies developed by an individual (prioritization/sequentialization of the tasks) to be determined.

Preferred but non-limiting aspects of the method according to the invention are the following:
the secondary task consists in the execution of an action in response to at least one visual and/or audio and/or tactile stimulus, the moment of generation of each stimulus during the step c) depending on a position in the actual movement corresponding to the execution of the primary task;
the step c) for evaluating third performance ratings comprises a sub-step consisting in:
Detecting a cycle in the actual movement based on measured first data values, and
Generating a stimulus for the execution of the secondary task at a given moment in the cycle,
Repeating the generation of the stimulus at each corresponding moment during successive cycles;
the step c) for evaluating third performance ratings comprises a sub-step consisting in:
Detecting various positions in the actual movement based on measured first data values,
Generating a stimulus for the execution of the secondary task at a given position,
Repeating the generation of the stimulus for various positions of the actual movement;
the step c) for evaluating third performance ratings comprises a sub-step consisting in:
Detecting a particular event in the execution of the primary task based on measured first data values,
Generating a stimulus for the execution of the secondary task upon a given event,
Repeating the generation of the stimulus for various events of the primary task;
the step a) for evaluating first performance ratings comprises a sub-step consisting in adjusting a level of difficulty of the primary task as a function of a score determined in association with the execution of the primary task;
the step for evaluating second performance ratings comprises a sub-step consisting in comparing the collected second data values with a response model for determining a score associated with the execution of the secondary task;
the step b) for evaluating second performance ratings comprises a sub-step consisting in adjusting a level of difficulty of the secondary task as a function of the score determined in association with the execution of the secondary task;
the step a) for evaluating first performance ratings comprises a sub-step consisting in comparing each measured first data value with at least one theoretical data value, so as to obtain a plurality of differences in correspondence representative of variations over time between the actual movement of the individual and a desired movement that the individual should have made;
the mobile terminal comprises three sensors consisting of a magnetometer, an accelerometer and a gyroscope, the sub-step for measuring a plurality of first data values consisting in measuring:
at least one linear acceleration with the accelerometer, and preferably three linear accelerations along three orthogonal axes, at least one angular velocity with the gyroscope, and preferably three angular velocities along the three orthogonal axes, at least one magnetic field with the magnetometer, and preferably three magnetic fields along the three orthogonal axes;

the sub-step consisting in determining an actual movement comprises the estimation of an orientation vector of the mobile terminal based on the first data values coming from the measurements of the accelerometer, of the magnetometer and of the gyroscope;

the method comprises, prior to the sub-step consisting in determining an actual movement, a sub-step consisting in filtering the measured first data values using a Kalman filter so as to eliminate interference due to measurement noise and errors;

the sub-step consisting in filtering the first data values comprises:
  the estimation of a first orientation vector based on the measurements from the accelerometer and from the magnetometer,
  the estimation of a second orientation vector based on the measurements from the gyroscope,
  the comparison of the first and second estimated orientation vectors and the use of their difference for updating the Kalman filter.

The invention also relates to a computer program product comprising a program code recorded on a data medium readable by a computer for executing the method according to any one of the preceding claims when the computer program is applied to a computer in order to be executed.

BRIEF DESCRIPTION OF THE DRAWINGS

Other advantages and features will become more clearly apparent from the description that follows of several variant embodiments, given by way of non-limiting examples, based on the appended drawing in FIG. 1 which illustrates one example of a method for evaluating an attentional demand or cost required for the execution of a task or the attention sharing strategies developed by an individual.

DETAILED DESCRIPTION OF THE INVENTION

Figure 1:
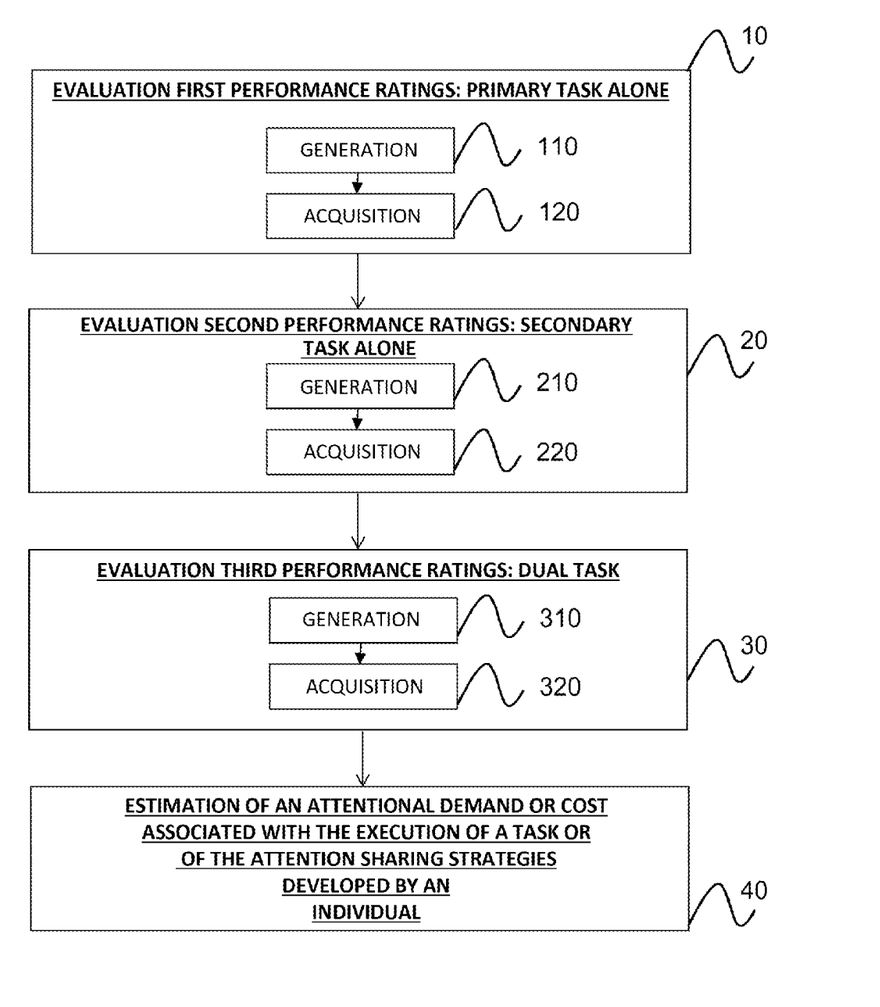

Preferred but non-limiting aspects of the present invention will now be described in more detail with reference to FIG. 1.

1. General Principles

The method according to the invention is dedicated to the estimation of the attentional resources required for the execution of a primary task or to the determination of the attention sharing strategies developed by an individual (prioritization/sequentialization of the tasks).

This method is based on the use of the dual-task paradigm consisting in making an individual execute independently and simultaneously primary and secondary tasks.

The primary and secondary tasks may consist of a proprioceptive task, or a motor task, or a perceptive task, or a postural task, or a locomotion task, or a locomotion task, or a spatial orientation task or a functional task, or a cognitive task, or a visuo-motor tracking task, or a visuo-manual pointing task, or a pedalling task, etc.

The primary task is for example:
a task for repositioning a body part,
a spatial orientation task,
a task for controlling the "sitting" or "standing" posture,
a task referred to as "TUG" (acronym for "Timed Up and Go") which consists in measuring the time that an individual takes to get up from a chair, walk three meters, turn round and sit down again,
a walking task,
a visuo-manual pointing task,
a pedalling task, etc.

The secondary task is for example:
a reaction time task,
an arithmetical task,
a memory task,
a counting down task,
a verbal fluency task,
spatial memory or inhibition tasks,
a visuo-motor tracking task,
a functional task (carrying a glass of water while trying not to spill it), etc.

This method may be implemented in the form of a downloadable application able to be implemented in a mobile terminal including:
display means such as a display screen,
inputting means such as a keyboard (potentially digital in the case of a terminal including a touch screen),
processing means such as a processor,
measurement means such as sensors, and notably an accelerometer and/or a magnetometer and/or a gyroscope,
sound or speech capturing means such as a microphone,
means for capturing user inputs such as a touch screen or a push button,
means of touch-sensitive and/or visual and/or audio alarm, such as a vibrator and/or the display screen and/or a loudspeaker.

The terminal additionally comprises connection means (wired or wireless) allowing the latter to be connected to one (or several) sensor(s) and/or external actuator(s) which could be necessary for the acquisition of certain data that cannot be acquired by means of sensor(s) and/or actuator(s) integrated into the terminal.

The mobile terminal also comprises storage means, such as a memory, for the storage of predefined tests or of exercises to be carried out by the individual. It may also comprise means for transmission/reception of signals, such as an antenna, for communicating with other fixed or mobile terminals in order to exchange information with third-parties.

The fact that the various means for the implementation of the method are embedded in a single device, such as a mobile terminal, facilitates the implementation of the method for the individual. It notably allows its use outside of a laboratory or of a hospital environment. Indeed, the only operation to be performed for the individual is to procure the mobile terminal. Thus, the implementation of the method may be carried out fully autonomously without the presence of a third-party (doctor, experimenter, researcher, trainer, etc.) thanks to its simplicity of use.

The mobile terminal is for example a portable telephone notably of the smartphone type, a PDA (abbreviation for "Personal Digital Assistant"), or any type of mobile terminal known to those skilled in the art, such as a connected watch of the Apple Watch® type.

Thus, an integrated solution is provided that allows the attentional resources or costs needed for the execution of a perceptive, postural, locomotion, motor, spatial orientation or functional task to be evaluated or the attention sharing strategies developed by an individual to be determined, based on the evaluation of the performance ratings obtained during the execution of two primary and secondary tasks carried out alone and separately, or simultaneously. This evaluation is useful for example to enable a quantification of the allocation/mobilization of the attentional resources needed for the execution of a primary task, so as to allow an evaluation of the capacity of the individual to move or to switch their attention onto two concurrent tasks, and/or in order to predict and prevent a risk of falling.

More precisely, the solution provided allows the following to be evaluated:
- the performance of the individual in the execution of one (or several) primary task(s)—of perceptive or postural or locomotion or motor or spatial orientation or functional nature—carried out alone,
- the performance of the individual in the execution of one (or several) secondary task(s)—of the reaction time or arithmetic or memorization or counting down or verbal fluency or spatial memory or inhibition or visuo-motor tracking or functional type, etc.—carried out alone,
- the performance of the individual in the simultaneous execution of the primary and secondary tasks described hereinabove.

These three evaluations allow the attentional resources or costs needed for the execution of the tasks of perceptive, postural, locomotion, motor, spatial orientation or functional nature to be estimated and/or the attention sharing strategies developed by an individual to be determined.

The results of these evaluations may subsequently be used to better measure and deal with the capacities for control of the balance, of the movement and of the locomotion of the individual, and for predicting the risk of a potential fall and to establish personalized strategies for prevention of falls.

Advantageously, the mobile terminal may be fixed onto a region of the individual in order to perform a particular measurement for a task.

The region in which the mobile terminal is fixed of course depends on the type of primary and secondary tasks that the individual has to perform.

2. Method

One example of a method will now be described with reference to the estimation of the attentional resources invoked during the execution of a task or to the determination of the attention sharing strategies developed by an individual (prioritization sequentialization of the tasks).

It is assumed that the individual has previously selected an exercise based on the dual-task paradigm that a practitioner has for example prescribed for them.

Once the exercise has been selected, the mobile terminal executes various phases 10, 20, 30:
- for evaluating first performance ratings of the individual when the latter carries out the primary task alone,
- for evaluating second performance ratings of the individual when the latter carries out the secondary task alone, and
- for evaluating third performance ratings of the individual when the latter carries out the primary task and the secondary task simultaneously.

Using the evaluations of first, second and third performance ratings, the method comprises a phase 40 for estimating the attentional resources required in order to perform the primary task or the attention sharing strategies developed by an individual.

Advantageously, a score representative of the attentional resources invoked or of the interferences or of prioritization/sequentialization of the tasks may be calculated. This score may be used to update a level of difficulty of the test or of the exercise and/or to add or to remove an exercise.

This score may also be sent to a third-party in order to allow them to monitor the variation over time in the attentional resources required by an individual, for example in the framework of a re-education in order to teach (or to re-teach) an individual to automate a postural, motor or locomotion task.

The quantification associated with the exercise carried out allows the progress of an individual in the execution of the exercise to be evaluated in terms of performance and of degree of automation. This quantification furthermore allows the levels of difficulty of the exercises to be updated.

These various phases will now be described in more detail with reference to the method illustrated in FIG. 1.

2.1. Evaluation of the First Performance Ratings

The phase 10 for evaluating first performance ratings comprises the steps consisting in:
- Generating 110 a first type of visual and/or audio and/or touch-sensitive information on the terminal, the said information including instructions relating to a primary task to be carried out,
- Measuring 120 a plurality of first data values with sensors of the mobile terminal during the execution of the primary task,
- Determining an actual movement of the individual with processing means of the mobile terminal, the actual movement being determined based on the measured first data values during the execution of the primary task.

In the framework of the present invention, the term "movement" is understood to mean the series of positions occupied by a point (or by a set of points) of one (or several) part(s) of the body of the individual (torso, thigh, leg, foot, etc.) in space over time. Thus, a "movement" may for example consist of a displacement according to a particular sequence of operations or, on the contrary, of the absence of a displacement. Commonly, a "movement" is represented by a set of vectors (for example "velocity vector" or "orientation vector") which each define the displacement of a point with respect to a fixed frame of reference in space and at a given moment in time.

2.1.1. Generation of a First Type of Information

The step 110 for generating a first type of information allows information on the primary task to be carried out to be provided to the individual. This first information may be displayed on the screen of the mobile terminal or be emitted via a loudspeaker of the terminal.

For the execution of a complex primary task, the information relating to its execution may be progressively provided to the individual as they carry out the said task.

For example, in the case of the execution of a primary task of the "TUG" type consisting in:
- getting up from a sitting position,
- walking 3 meters,
- turning around
- returning to the initial position and
- sitting back down, information indicating to the individual to return to their initial position and to sit back down may, for example, be sent while the individual is walking. This information may be generated in visual, audio or touch-sensitive form (by means of the vibrator of the mobile terminal).

2.1.2. Measurement of First Data

In one step, the phase for evaluation of the first performance ratings comprises the measurement 120, by sensors of the mobile terminal, of a plurality of first data values representing the movement or the absence of movement given as a target instruction. The step 120 for measuring the first data values is carried out during the execution of the primary task.

The first data values may be measured by means of sensors of the mobile terminal. For example, if the mobile terminal comprises a 3D accelerometer, a 3D magnetometer and a gyroscope:
- three of the measured first data values may correspond to linear accelerations along three orthogonal axes,
- three of the measured first data values may correspond to angular velocities along the same three orthogonal axes, and
- three of the measured first data values may correspond to magnetic fields along the same three orthogonal axes.

These first data values measured by the various sensors may subsequently be merged in order to determine the actual movement of the individual.

The use of groups of first data values each composed of measurements coming from an accelerometer, from a magnetometer and from a gyroscope allows the precision in the estimation of the actual movement performed by the individual to be improved.

2.1.3. Filtering of the Measured First Data Values

The method may also comprise an optional step for filtering the groups of first data values measured using the sensors of the mobile terminal. This allows the interference due to noise and to the measurement errors to be eliminated.

Advantageously, the filtering of the groups of first data values may be implemented using a filter of the Kalman type.

This type of filter is particularly adapted to the estimation of parameters of a system varying over time based on raw measurements, which is the case in the framework of the present invention since the various groups of first data values are signals representative of a movement performed by the individual.

Thus, each group of first data values carries information on:
- the position of the mobile terminal at a given moment in time,
- the orientation of the mobile terminal at the given moment in time, and
- the speed of displacement of the mobile terminal at the given moment in time.

2.1.4. Determination of the Actual Movement of the Individual

Using these measured first data values, it is possible to determine the movement of one (or several) point(s) of the individual.

More precisely, the processor of the mobile terminal processes the groups of measured first data values in order to extract the information relating to the position and/or the orientation and/or the speed of displacement of the mobile terminal at the various measurement moments over a period of time.

A series of data values estimated at the various moments within the period of time is thus obtained, this series being representative of the actual movement of the individual during the period of time.

Depending on the type of exercise, only certain parameters of the movement performed by the individual may need to be monitored. For example, for some exercises, the speed of displacement is not a determinant criterion. In this case, no estimated data relating to a speed of displacement will be calculated from the groups of first data values.

This allows:
- the hardware resources invoked (notably memory space), and
- the energy consumed by the mobile terminal for implementing the method to be limited.

The actual movement thus determined may form a reference in the execution of the primary task. In this case, the first performance ratings consist of this actual movement determined.

As a variant, the actual movement determined may be compared with a theoretical movement that the individual should "ideally" carry out, as described in the French Patent application dated 20 Nov. 2014 and filed under the number 1461233. In this case, the method may comprise an additional step consisting in calculating a score relating to the execution of the primary task, notably as a function of the difference (or differences) between the actual and theoretical movements. In this case, the calculated score constitutes the evaluated first performance ratings.

These first performance ratings may subsequently be compared with the third performance ratings of the individual during the simultaneous execution of the primary and secondary tasks, in order to estimate the attentional demand required by the individual for the control of their movements.

2.2. Evaluation of the Second Performance Ratings

The phase 20 for evaluation of the second performance ratings comprises the steps consisting in:
- Generating 210 a second type of visual and/or audio and/or touch-sensitive information on the terminal, the said information including instructions relating to a secondary task to be carried out,
- Collecting 220 second data values representing the response of the individual during the execution of the secondary task,
- Comparing the collected second data values with a response model so as to determine a score associated with the execution of the secondary task.

This phase allows the performance ratings of the individual when the latter only carries out the secondary task to be evaluated.

2.2.1. Generation of a Second Type of Information

The step 210 for generation of a second type of information allows information on the secondary task to be performed to be supplied to the individual. This second information may be displayed on the screen of the mobile terminal or be emitted via a loudspeaker of the terminal.

The secondary task may, in some applications, consist of an action to be carried out in response to a stimulus—for example visual (flashing light on the display screen of the mobile terminal) or audio (audio beep emitted from the loudspeaker of the mobile terminal) or touch-sensitive (activation of a vibrator of the mobile terminal), etc.

In this case, the stimulus (or stimuli) are generated progressively during the execution of the secondary task.

2.2.2. Collection of the Second Data Values

The step 220 for collecting second data values is carried out during the execution of the secondary task.

These second data values may comprise:
- a reaction time,
- a response input written on the keyboard of the terminal (selection of a response from amongst a multiple choice, etc.),
- an oral response detected by a microphone of the mobile terminal,
- a choice from amongst a plurality of possible responses,
- a spatial displacement (or orientation) of the mobile terminal in response to a stimulus, an actuation of a push button of the (or connected to the) terminal, etc.

These second data values may be collected using various sensors of the terminal as previously described with reference to the phase of evaluation of the first performance ratings.

Advantageously, the moment of generation of the second information may depend on the cycle of execution of the primary task.

2.2.3. Comparison

The collected second data values may subsequently be compared with an "ideal" model response in order to determine a score for the exercise.

For example, if the secondary task consists in counting down in sevens starting from one hundred (100, 93, 86, 79, 72, . . . . , 9, 2) out loud, the terminal will have detected via its microphone the succession of responses provided by the individual and will be able to compare them with the solution to this exercise.

Based on this comparison, a score may be calculated for the secondary task carried out.

Advantageously, the level of difficulty of the secondary task may be adapted as a function of the score obtained by the individual following the completion of the task. This allows the level of difficulty of the secondary task to be normalized according to the capacities of the individual.

For example, if it turns out that the individual does not have sufficient cognitive capacities to perform the secondary mental arithmetic task consisting in counting down in sevens starting from a hundred, then the level of difficulty of the secondary task may be reduced (counting down in 5 s starting from 100, etc.).

If, on the contrary, the score of the individual is maximum, the level of difficulty of the secondary task may be increased.

Indeed, in order that the attentional resources associated with the execution of a primary task can be estimated, it is necessary for the individual to be capable of carrying out the secondary task. However, it is preferable for the level of difficulty of this secondary task to be sufficiently high so as to be able to detect an influence of this secondary task on the execution of the primary task. This allows a level of interference between the primary and secondary tasks to be obtained which has an impact on the behavioral performance of the individual and makes the attentional cost of the primary task measurable.

2.3. Evaluation of the Third Performance Ratings

For the evaluation 30 of the third performance ratings, the primary and secondary tasks are carried out simultaneously by the individual. The phase for evaluation of the third performance ratings comprises the steps consisting in:

- Generating 310 a third visual and/or audio and/or touch-sensitive type of information on the terminal, the said information including instructions relating to the simultaneous execution of the primary task and of the second secondary task,
- Measuring 320 the third data values (which may consist in reaction times, angles, responses, etc.) relating to the execution of the primary and secondary tasks.

The third information comprises a target instruction associated with the simultaneous execution of the primary and secondary tasks. Depending on this target instruction (in other words the priority for the primary task, priority for the secondary task, no priority), the method allows:

- either the attentional resources required for the execution of the primary task to be estimated,
- or the effect (beneficial or negative) of the execution of the secondary task on the primary task to be estimated,
- or the attention sharing strategy developed by an individual to be estimated.

Notably, the target instruction may consist in inviting the individual to carry out the primary task with a higher priority (and if possible with the same level of performance as when the primary task was carried out on its own), the concurrent secondary task having to be performed as well as possible. In this case, the method allows the attentional requirement or cost associated with the execution of the primary task to be determined. Indeed, when the attentional capacities of the central nervous system are exceeded, due to the concurrence between the primary and secondary tasks, the performance in the secondary task decreases. This drop in performance in the secondary task takes into account the attentional cost needed to carry out the primary task.

The target instruction may consist in asking the individual to carry out the secondary task with a higher priority (and if possible with the same level of performance as when the secondary task was carried out on its own). In this case, the method allows the effects (beneficial or negative) of a secondary task on the control mechanisms involved in the execution of the primary task to be determined.

As a variant, the target instruction may lastly consist in asking them to carry out the primary and secondary tasks simultaneously without asking them to maintain the level of performance of one or the other of the primary and secondary tasks (in other words without a target instruction on priority for the primary or secondary task). Thus, either a degradation of the two tasks, or a degradation of only one or the other of the primary and secondary tasks is observed. This degradation is representative of the priority given by the individual to one or the other of the primary and secondary tasks. The method then allows the attention sharing strategies developed by the individual to be identified.

Since the steps for generation and for measurement/collection of the third phase of the method are similar to the steps for generation and for measurement/collection described with reference to the phases for evaluation of the first and second performance ratings, the latter will not be described in more detail here.

Advantageously, when the secondary task consists in carrying out an action in response to a stimulus, the moment of generation of the stimulus may be dependent on the primary task.

For example, if the tasks to be executed consist:
for the primary task: in walking, and
for the secondary task: in producing a sound out loud in response to an audio stimulus, such as a "beep" (task for reaction time to an audible stimulus),
then each audio stimulus may be emitted when the individual is simply resting (i.e. on a foot) during their walking cycle. As a variant, each stimulus may be emitted each time that the two feet of the individual rest on the ground during their walking cycle.

By way of a non-limiting illustrative example, the method may comprise the following sub-steps for taking into account the primary task in the presentation of the secondary task:
Detecting one cycle in the execution of the primary task using the measured data,
Generating a stimulus for the execution of the secondary task at a given moment in the cycle,
Repeating the generation of the stimulus at each corresponding moment during successive cycles of the execution of the primary task.

The third data values measured during the simultaneous execution of the primary and secondary tasks are compared with the first and second data values obtained during the separate execution of the said primary and secondary tasks. In the situation where scores have been calculated for each of these tasks carried out separately and simultaneously, these scores may be compared with one another. In the case of multiple measurements, statistics on the distributions of the data could be added.

2.4. Estimation of the Attentional Resources Invoked/Determination of an Attention Sharing Strategy Developed by an Individual The comparison of the data measured and collected during the various phases of evaluation allows:
either the attentional demand required for the execution of the primary task,
or the attention sharing strategy developed by an individual (prioritization/sequentialization of the tasks) to be estimated 40.
This comparison allows:
an improvement in the dual-task performance ratings, or conversely
a deterioration in the dual-task performance ratings in the execution of one or the other of the tasks (or of both tasks) to be observed.

This estimation step 40 offers numerous advantages. Indeed, it allows for example:
the progression of an individual in the framework of a re-education consisting in re-teaching them to automate a motor task such as walking to be evaluated
an individual to be alerted of a potential risk of a fall when their attentional resources are no longer sufficient for executing a motor or functional task appropriately.

The study of the modifications of the characteristics of a primary task under dual-task conditions therefore allows the study of the physiological and pathological disorders associated with the execution of this task.

Aside from a better understanding of the mechanisms of disorganization of the motor control, this new approach allows the development of a series of clinical tests for predicting falls and of re-education techniques.

3. Examples of Use

Two examples using the method described hereinabove will now be presented.

In these two examples, the presentation of the secondary task (for example, the triggering of a stimulus or generation of a question) is controlled by the detection of an event in the primary task.

3.1. First Example

The "Time Up and Go" (TUG) is a test of functional mobility used in the evaluation and the monitoring of the re-education of the elderly and of patients notably exhibiting neurological, orthopedic or else traumatological impairments.

For this relatively easy and quick test, the person is asked to get up from an armchair, to take a step, to turn around and to go back and sit down, in other words to carry out common varied postural and locomotion tasks of daily life.

Using the signals produced by inertial sensors contained in a mobile terminal of the "smartphone" type and/or connected to the terminal, it is possible to identify these various phases.

The solution provided in the present application offers the possibility of presenting a secondary task—such as a cognitive task (triggering of an audible stimulus for a reaction time task for example)—as a function of the postural and locomotion tasks (sitting, standing, stepping, etc.) associated with the execution of the TUG test, which advantageously allows the attentional cost associated with the performance of each of these postural and locomotion tasks to be determined.

3.2. Second Example

Walking is conventionally described as a succession of:
i) dual resting (the two feet are on the ground),
ii) single resting (only one foot on the ground). Two different phases are distinguished:
i) the resting phase corresponding to the entire period where the foot is in contact with the ground (this resting phase starts by posing the heel on the ground and finishes with lifting the big toe off the ground), and
ii) the swinging phase where the foot is no longer in contact with the ground and which corresponds to the advance of the lower member (this swinging phase starts by lifting the big toe off the ground and finishes with the posing of the heel on the ground). For a young person in good health, the resting phase occupies 60% of the walking cycle and the swinging phase 40%.

The walking cycle may be divided into several successive periods:
i) the first period is a dual resting phase during which the weight of the body will be transferred onto a lower member; this lasts for 10% of the cycle;
ii) the second period is the single resting phase which lasts for 40% of the cycle;
iii) the third period is a new dual resting phase lasting for 10%;
iv) the fourth period is a swinging phase without contact with the ground lasting for 40%.

Thus, one complete cycle comprises 2 dual resting phases, one monopodal resting phase and one swinging phase.

Using the signals produced by the inertial sensors contained in a mobile terminal of the "smartphone" type and/or connected to the mobile terminal, it is possible to identify these various periods and phases.

The solution provided in the present application offers the possibility of presenting a secondary task—such as a cognitive task (triggering of an audible stimulus for a reaction time task for example)—as a function of the walking phases (for example, initiation of the step, single resting, dual resting, etc.), which advantageously allows the attentional cost associated with the execution of each of these phases to be determined.

Advantageously, the difficulty of the secondary task (and/or of the primary task) may be modified on line as a function of data collected on the primary task or the secondary task.

4. Conclusion

The use of the dual-task paradigm highlights the close relationships that exist between the sensori-motor and cognitive processes.

The dual-task training is appropriate notably in individuals at the initial phase of dementia. By simultaneously placing demands on the sensori-motor and cognitive functions of these persons, this treatment allows their autonomy and their quality of life to be improved, notably their capacities to be able to carry out the activities of everyday life as well as possible, and to prevent the risk of falling.

It goes without saying that this dual-task training may have numerous applications for other types of individuals (children, elderly people, injured people, sports people, etc.).

Fragile elderly individuals likely to fall and exhibiting walking disorders may benefit from dual-task types of exercises in order to enable them to improve their walking automation. The same is true for individuals exhibiting cognitive disorders.

By using a mobile terminal such as provided in the framework of the present invention, it is possible to improve the effectiveness of the dual-task training by offering exercises adapted to each individual, and by facilitating the implementation of these exercises.

In contrast to the existing solutions, the present invention allows target instruction parameters to be set up. It furthermore allows it to be determined whether the individual has been able to achieve the target parameters set by the analysis of the data acquired via the sensors.

These elements—together with the other features previously described—allow the solution according to the present invention to be usable in complete autonomy without requiring the assistance of a third-party.

It goes without saying that the present invention is not strictly limited to the implementation of two tasks for estimating an attentional demand or cost or of an attention sharing strategy developed by an individual. Indeed, the method according to the invention may be implemented with more than two tasks (for example, three, four, five tasks, etc.) carried out separately and simultaneously.

The invention claimed is:

1. A method for estimating an attentional demand or cost associated with the execution of a task or of an attention sharing strategy developed by an individual, said method being implemented in a mobile terminal and being based on the use of a multi-task paradigm, characterized in that it comprises the following steps:

generating, via at least one of a touch-sensitive, visual, or audio alarm of said mobile terminal, a first type of one or more visual, audio, or touch-sensitive information on the mobile terminal, said first type of one or more visual, audio, or touch-sensitive information including first instructions relating to the at least one primary task to be carried out alone;

measuring, by a plurality of sensors on said mobile terminal including an accelerometer, a gyroscope, and a magnetometer, a plurality of first data values during execution of the at least one primary task alone, wherein measuring the plurality of first data values comprises measuring at least one linear acceleration with the accelerometer, at least one angular velocity with the gyroscope, and at least one magnetic field with the magnetometer;

determining, by a processor of said mobile terminal, an actual movement of the individual, the actual movement being determined based on the plurality of first data values measured by the plurality of sensors during the execution of the at least one primary task;

determining, by said mobile terminal, first performance ratings based on the first data values, the first performance ratings associated with execution of the at least one primary task alone;

generating, via at least one of the touch-sensitive, visual, or audio alarm of said mobile terminal, a second type of one or more visual, audio, or touch-sensitive information on the mobile terminal, said second type of one or more visual, audio, or touch-sensitive information including second instructions relating to the at least one secondary task to be carried out alone at a first level of difficulty;

collecting, by one or more sensors of said mobile terminal, second data values representing the response of the individual during execution of the at least one secondary task alone at the first level of difficulty;

comparing, by said mobile terminal, the second data values with a response model;

determining, by said mobile terminal, a score associated with the execution of the at least one secondary task at the first level of difficulty based on the comparing, wherein a level of difficulty of the at least one secondary task is modified from the first level of difficulty to a second level of difficulty based on the score;

subsequent to the level of difficulty of the at least one secondary task being modified, generating, via at least one of the touch-sensitive, visual, or audio alarm of said mobile terminal, an updated second type of one or more visual, audio, or touch-sensitive information on the mobile terminal, said updated second type of one or more visual, audio, or touch-sensitive information including updated second instructions relating to the at least one secondary task to be carried out alone at the second level of difficulty;

collecting, by the one or more sensors of said mobile terminal, updated second data values representing the response of the individual during execution of the at least one secondary task alone at the second level of difficulty, wherein each of the at least one primary task, the at least one secondary task at the first level of difficulty, and the at least one secondary task at the second level of difficulty are carried out separately according to the first instructions, the second instructions, and the updated second instructions;

determining, by said mobile terminal, second performance ratings based on the updated second data values, the second performance ratings associated with execution of the at least one secondary task at the second level of difficulty alone;

generating, via at least one of the touch-sensitive, visual, or audio alarm of said mobile terminal, a third type of one or more visuals audio, or touch-sensitive information on the mobile terminal, said third type of one or more visual, audio, or touch-sensitive information including third instructions relating to simultaneous execution of the at least one primary task and the at least one secondary task at the second level of difficulty;

measuring, by a measurement unit of said mobile terminal, third data values relating to the simultaneous execution of the at least one primary task and the at least one secondary task at the second level of difficulty;

determining, by said mobile terminal, third performance ratings based on the third data values, the third performance ratings associated with simultaneous execution of the at least one primary task and the at least one secondary task at the second level of difficulty;

comparing, by said mobile terminal, the first, second and third performance ratings for one or more of:

estimating the attentional demand required for the execution of the at least one primary task, estimating an effect of the at least one secondary task on control mechanisms involved in the execution of the at least one primary task, or estimating the attention sharing strategy developed by the individual.

2. The method as claimed in claim 1, in which the at least one secondary task consists in the execution of an action in response to at least one visual, audio, or tactile stimulus, a moment of generation of each stimulus during the simultaneous execution of the at least one primary task and the at least one secondary task depending on a position in the actual movement corresponding to the execution of the at least one primary task.

3. The method as claimed in claim 1, in which the simultaneous execution of the at least one primary task and the at least one secondary task comprises a sub-step consisting in:

detecting a cycle in the actual movement based on the plurality of first data values; and generating a stimulus for the execution of the at least one secondary task at a given moment in the cycle; and repeating the generation of the stimulus at each corresponding moment during successive cycles.

4. The method as claimed in claim 1, in which the simultaneous execution of the at least one primary task and the at least one secondary task comprises a sub-step consisting in:

detecting various positions in the actual movement based on the plurality of first data values;

generating a stimulus for the execution of the at least one secondary task at a given position; and repeating the generation of the stimulus for the various positions of the actual movement.

5. The method as claimed in claim 1, in which the simultaneous execution of the at least one primary task and the at least one secondary task comprises a sub-step consisting in:

detecting a particular event in the execution of the at least one primary task based on the plurality of first data values;

generating a stimulus for the execution of the at least one secondary task upon a given event; and repeating the generation of the stimulus for various events of the at least one primary task.

6. The method as claimed in claim 1, further comprising adjusting a level of difficulty of the at least one primary task as a function of a score determined in association with the execution of the at least one primary task.

7. The method as claimed in claim 1, further comprising comparing each of the plurality of first data value with at least one theoretical data value, so as to obtain a plurality of differences in correspondence representative of variations over time between the actual movement of the individual and a desired movement that the individual should have made.

8. The method as claimed in claim 1, wherein the determining the actual movement comprises an estimation of an orientation vector of the mobile terminal based on the plurality of first data values coming from the measurements of the accelerometer, of the magnetometer and of the gyroscope.

9. The method as claimed in claim 8, further comprising, prior to determining the actual movement, filtering the plurality of first data values using a Kalman filter so as to eliminate interference due to the measurement noise and errors.

10. The method as claimed in claim 9, wherein the filtering the plurality of first data values comprises:

estimating a first orientation vector based on the measurements from the accelerometer and from the magnetometer;

estimating a second orientation vector based on the measurements of the gyroscope; and comparing the estimated first and second orientation vectors and the use of their difference for updating the Kalman filter.

11. A computer program product comprising a program code recorded on a non-transitory data medium readable by a computer for executing the method as claimed in claim 1, when the computer program is applied to the computer in order to be executed.

12. The method of claim 1, further comprising:

predicting, based on the comparing of the first, second, and third performance ratings, a risk of a potential fall for the individual; and alerting the individual of the risk of a potential fall based on the predicting.

13. The method of claim 1, wherein the third instructions comprises a priority for the at least one primary task during the simultaneous execution of the at least one primary task and the at least one secondary task at the second level of difficulty or a priority for the at least one secondary task at the second level of difficulty during the simultaneous execution of the at least one primary task and the at least one secondary task at the second level of difficulty.

* * * * *